US010157265B1

(12) United States Patent
Darnell

(10) Patent No.: US 10,157,265 B1
(45) Date of Patent: Dec. 18, 2018

(54) CLINICAL STUDY PRODUCT DISPENSING DEVICE

(71) Applicant: RAI Strategic Holdings, Inc., Winston-Salem, NC (US)

(72) Inventor: John H. Darnell, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 0 days.

(21) Appl. No.: 15/711,529

(22) Filed: Sep. 21, 2017

(51) Int. Cl.
*G06F 19/00* (2018.01)
*A61J 7/04* (2006.01)

(52) U.S. Cl.
CPC ......... *G06F 19/3462* (2013.01); *A61J 7/0427* (2015.05); *A61J 7/0463* (2015.05); *A61J 7/0481* (2013.01); *G06F 19/36* (2013.01)

(58) Field of Classification Search
CPC .... G06F 19/3462; G06F 19/36; A61J 7/0481; A61J 7/0463; A61J 7/0427
USPC ................................................. 700/231–244
See application file for complete search history.

(56) References Cited

U.S. PATENT DOCUMENTS

| 2,057,353 | A | 10/1936 | Whittemore, Jr. |
| 2,104,266 | A | 1/1938 | McCormick |
| 3,200,819 | A | 8/1965 | Gilbert |
| 4,497,874 | A | 2/1985 | Hale |
| 4,735,217 | A | 4/1988 | Gerth et al. |
| 4,793,365 | A | 12/1988 | Sensabaugh, Jr. et al. |

(Continued)

FOREIGN PATENT DOCUMENTS

| CN | 1541577 | 11/2004 |
| CN | 2719043 | 8/2005 |

(Continued)

OTHER PUBLICATIONS

"Automated medication dispensing solution (Automatic Pill Dispenser), shows high rates of medication adherence and potential to reduce cost of care" E-Pill LLC. Retrieved Jul. 2017; pp. 1-14.

(Continued)

*Primary Examiner* — Michael Collins
(74) *Attorney, Agent, or Firm* — Womble Bond Dickinson (US) LLP

(57) ABSTRACT

A dispensing device and a method of operating a dispensing device for use in studying a consumable unit used by a clinical study participant are provided. The device comprises a housing that includes a delivery aperture and a compartment configured to store an unconsumed consumable unit therein. The device further includes a dispensing mechanism located within the housing and configured to release the stored unconsumed consumable unit to the clinical study participant via the delivery aperture upon verifying the identity of the clinical study participant and a controller configured to interface with the dispensing mechanism and the user input device. A user input device is also included and is configured to receive input from the clinical study participant corresponding to identification information relating to the clinical study participant and is further configured to receive input from the clinical study participant in response to one or more questionnaires relating to consumption of the consumable unit.

22 Claims, 9 Drawing Sheets

(56) References Cited

U.S. PATENT DOCUMENTS

| | | | |
|---|---|---|---|
| 4,922,901 A | 5/1990 | Brooks et al. | |
| 5,060,671 A | 10/1991 | Counts et al. | |
| 5,093,894 A | 3/1992 | Deevi et al. | |
| 5,101,839 A | 4/1992 | Jakob et al. | |
| 5,154,192 A | 10/1992 | Sprinkel et al. | |
| 5,261,424 A | 11/1993 | Sprinkel, Jr. | |
| 5,372,148 A | 12/1994 | McCafferty et al. | |
| 5,388,574 A | 2/1995 | Ingebrethsen et al. | |
| 5,505,214 A | 4/1996 | Collins et al. | |
| 5,530,225 A | 6/1996 | Hajaligol | |
| 5,687,746 A | 11/1997 | Rose et al. | |
| 5,713,485 A | 2/1998 | Liff et al. | |
| 5,726,421 A | 3/1998 | Fleischhauer et al. | |
| 5,865,185 A | 2/1999 | Collins et al. | |
| 5,894,841 A | 4/1999 | Voges | |
| 5,934,289 A | 8/1999 | Watkins et al. | |
| 5,954,979 A | 9/1999 | Counts et al. | |
| 5,967,148 A | 10/1999 | Harris et al. | |
| 6,040,560 A | 3/2000 | Fleischhauer et al. | |
| 6,125,082 A | 9/2000 | Reid | |
| 6,125,853 A | 10/2000 | Susa et al. | |
| 6,155,268 A | 12/2000 | Takeuchi | |
| 6,696,924 B1* | 2/2004 | Socinski | G06F 19/3456 700/213 |
| 6,772,756 B2 | 8/2004 | Shayan | |
| 6,779,531 B1 | 8/2004 | Biggs et al. | |
| 6,973,371 B1 | 12/2005 | Benouali | |
| 7,040,314 B2 | 5/2006 | Nguyen et al. | |
| 7,117,867 B2 | 10/2006 | Cox et al. | |
| 7,139,639 B2 | 11/2006 | Broussard et al. | |
| 7,483,839 B2* | 1/2009 | Mayaud | G06F 19/3456 705/2 |
| 7,726,320 B2 | 6/2010 | Robinson et al. | |
| 7,832,410 B2 | 11/2010 | Hon | |
| 8,205,622 B2 | 6/2012 | Pan | |
| 8,314,591 B2 | 11/2012 | Terry et al. | |
| 8,365,742 B2 | 2/2013 | Hon | |
| 8,402,976 B2 | 3/2013 | Fernando et al. | |
| 8,423,181 B2 | 4/2013 | Hallin | |
| 8,499,766 B1 | 8/2013 | Newton | |
| 8,528,569 B1 | 9/2013 | Newton | |
| 8,539,959 B1 | 9/2013 | Scatterday | |
| 8,554,365 B2 | 10/2013 | Thomas et al. | |
| 8,588,964 B2 | 11/2013 | Garda et al. | |
| 8,606,595 B2* | 12/2013 | Udani | G06Q 10/105 705/2 |
| 8,910,639 B2 | 12/2014 | Chang et al. | |
| 2002/0032582 A1* | 3/2002 | Feeney, Jr. | G06F 19/3462 705/2 |
| 2002/0042725 A1* | 4/2002 | Mayaud | G06F 19/3456 705/2 |
| 2004/0117062 A1* | 6/2004 | Bonney | A61M 15/0045 700/237 |
| 2005/0016550 A1 | 1/2005 | Katase | |
| 2005/0154491 A1* | 7/2005 | Anderson | A61M 15/00 700/236 |
| 2005/0251289 A1* | 11/2005 | Bonney | A61M 15/00 700/244 |
| 2006/0196518 A1 | 9/2006 | Hon | |
| 2007/0267031 A1 | 11/2007 | Hon | |
| 2008/0092912 A1 | 4/2008 | Robinson et al. | |
| 2009/0095311 A1 | 4/2009 | Hon | |
| 2009/0126745 A1 | 5/2009 | Hon | |
| 2009/0188490 A1 | 7/2009 | Hon | |
| 2009/0230117 A1 | 9/2009 | Fernando et al. | |
| 2009/0272379 A1 | 11/2009 | Thorens et al. | |
| 2010/0028766 A1 | 2/2010 | Peckerar et al. | |
| 2010/0163063 A1 | 7/2010 | Fernando et al. | |
| 2011/0094523 A1 | 4/2011 | Thorens et al. | |
| 2011/0126848 A1 | 6/2011 | Zuber et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2011/0290248 A1 | 12/2011 | Schennum | |
| 2012/0111347 A1 | 5/2012 | Hon | |
| 2012/0260927 A1 | 10/2012 | Liu | |
| 2012/0279512 A1 | 11/2012 | Hon | |
| 2013/0008457 A1 | 1/2013 | Zheng et al. | |
| 2013/0037041 A1 | 2/2013 | Worm et al. | |
| 2013/0056013 A1 | 3/2013 | Terry et al. | |
| 2013/0180553 A1 | 7/2013 | Gaus et al. | |
| 2013/0192623 A1 | 8/2013 | Tucker et al. | |
| 2013/0255702 A1 | 10/2013 | Griffith, Jr. et al. | |
| 2013/0298905 A1 | 11/2013 | Levin et al. | |
| 2013/0306084 A1 | 11/2013 | Flick | |
| 2014/0000638 A1 | 1/2014 | Sebastian et al. | |
| 2014/0060554 A1 | 3/2014 | Collett et al. | |
| 2014/0060555 A1 | 3/2014 | Chang et al. | |
| 2014/0096781 A1 | 4/2014 | Sears et al. | |
| 2014/0096782 A1 | 4/2014 | Ampolini et al. | |
| 2014/0209105 A1 | 7/2014 | Sears et al. | |
| 2014/0253144 A1 | 9/2014 | Novak et al. | |
| 2014/0261408 A1 | 9/2014 | DePiano et al. | |
| 2014/0261486 A1 | 9/2014 | Potter et al. | |
| 2014/0261487 A1 | 9/2014 | Chapman et al. | |
| 2014/0261495 A1 | 9/2014 | Novak et al. | |
| 2014/0270727 A1 | 9/2014 | Ampolini et al. | |
| 2014/0270729 A1 | 9/2014 | DePiano et al. | |
| 2014/0270730 A1 | 9/2014 | DePiano et al. | |
| 2016/0287480 A1 | 10/2016 | Hancock et al. | |
| 2017/0020191 A1 | 1/2017 | Lamb et al. | |
| 2017/0262614 A1* | 9/2017 | Vishnubhatla | G06F 19/328 |

FOREIGN PATENT DOCUMENTS

| | | |
|---|---|---|
| CN | 201379072 | 1/2010 |
| EP | 0 295 122 | 12/1988 |
| EP | 0 845 220 | 6/1998 |
| EP | 1 618 803 | 1/2006 |
| GB | 2469850 | 11/2010 |
| WO | WO 2003/034847 | 5/2003 |
| WO | WO 2004/080216 | 9/2004 |
| WO | WO 2005/099494 | 10/2005 |
| WO | WO 2007/131449 | 11/2007 |
| WO | WO 2016/164187 | 10/2016 |

OTHER PUBLICATIONS

Pleshek, "RFID: the cure for the clinical trial blues", Terso Solutions, Inc., 2011, pp. 1-7.

* cited by examiner

CLINICAL STUDY PRODUCT DISPENSING DEVICE

TECHNOLOGICAL FIELD

The present disclosure relates to a product dispensing device for use in a clinical study, and more particularly a product dispensing device for use in a clinical study that is configured to dispense one or more consumable units and record data in a controlled and secure manner. The device is also configured to receive input from a clinical study participant in response to one or more questionnaires relating to consumption of the consumable unit.

BACKGROUND

In various instances, it may be desired to dispense products, such as products that are regulated by a governmental agency, for example, certain foods, pharmaceutical drugs, medical devices, radiation-emitting products, vaccines, cosmetics, and/or tobacco products, in a controlled manner. To this end, numerous devices have been proposed that provide controlled dispensing of such products. See, for example, the various medication dispensing devices described in U.S. Pat. No. 5,713,485 to Liff et al., U.S. Pat. No. 7,139,639 to Broussard et al., U.S. Pat. No. 8,423,181 to Hallin, U.S. Pat. No. 8,554,365 to Thomas et al., and U.S. Pat. No. 8,588,964 to Garda et al., and the timed cigarette dispenser described in U.S. Pat. No. 6,125,082 to Reid, all of which are incorporated herein by reference in their entireties.

Some of these products may be administered according to a prescription, which designates the user and a prescription schedule. Other products may be the subject of a clinical study in conjunction with the use and/or manufacturing of the product. In certain applications, clinical studies are designed to investigate whether the product is safe for use by the general public. In other applications, clinical studies are used to determine the effectiveness and/or results of the consumption of the product. In any event, clinical studies are typically conducted under strict clinical study protocols that describe specific parameters surrounding the studies. Such parameters may include, for example, the identity or designation of a clinical study participant, the timing of consumption of the product, and the type of data that will be collected during the clinical study. In many instances, the data collected during the clinical study may include data collected directly from a clinical study participant in the form of answers to one or more questions relating to the product and/or the clinical trial study participant's experience with the product.

In many cases, the effectiveness of a product, or the efficacy of a clinical study relating to a product, may be dependent upon strict adherence to the prescription or the clinical study protocol. This may include, for example, verifying that the properly designed user uses the product and/or controlling use of the product according to the schedule. To this end, devices have been proposed that monitor the administering of such products. See, for example, the unit dose medication compliance device described in U.S. Pat. No. 6,973,371 to Benouali, and the portable pill dispenser described in U.S. Patent Application Publication No. 2016/0287480 to Hancock et al., both of which are incorporated herein by reference in their entireties.

It would be desirable, however, to provide further control, monitoring, and data gathering relating to the use of such products. For example, in the case of a product that is the subject of the clinical study, it is often advantageous to collect data from the study participant at pre-set checkpoints during the study. Many clinical studies, however, are conducted over a relatively lengthy period of time, and it is not reasonable to confine a clinical study participant to a single location in a controlled environment. As such, these clinical studies rely on the study participant taking responsibility for following the study protocol and remembering to submit answers to questions relating to the study participant's experience with the product at the specified checkpoints called out in the protocol. There is a need, therefore, for a clinical study product dispensing device that addresses at least some of these issues.

BRIEF SUMMARY

In various implementations, the present application provides a dispensing device for use in studying a consumable unit used by a clinical study participant. In one example implementation, the device comprises a housing that a includes a delivery aperture and a compartment configured to store an unconsumed consumable unit therein, a user input device configured to receive input from the clinical study participant corresponding to the identity of the clinical study participant, a dispensing mechanism located within the housing and configured to release the stored unconsumed consumable unit to the clinical study participant via the delivery aperture upon verification of the identity of the clinical study participant, and a controller configured to interface with the dispensing mechanism and the user input device. The user input device is further configured to receive input from the clinical study participant in response to one or more questionnaires relating to consumption of the consumable unit.

Some implementations further comprise a reader located in the housing configured to gather data from the unconsumed consumable unit. In some implementations, the housing further includes a spent unit aperture and a second compartment configured to receive at least a portion of a consumed consumable unit via the spent unit aperture. Some implementations further comprise a reader located in the housing and configured to gather data from the consumed consumable unit. In some embodiments, the input corresponding to the identity of the clinical study participant comprises a user number or access code. In some implementations, the consumable unit comprises an aerosol delivery device. In some implementations, the controller is further configured to control the dispensing mechanism according to a clinical study protocol. In some implementations, the user input device further comprises a display configured to display information to the clinical study participant. In some implementations, the information conveyed to the clinical study participant includes the one or more questionnaires relating to consumption of the consumable unit. In some implementations, the controller is further configured to control transfer of data to a remote device. In some implementations, the device is configured to be handheld. Some implementations further comprise a rechargeable battery configured to provide power to the dispensing mechanism, the user input device, and the controller.

In various implementations, the present application also provides a method of operating a storage and dispensing device for use in studying a consumable unit used by a clinical study participant. In one example implementation, the method comprises storing an unconsumed consumable unit inside a compartment of a housing that includes a delivery aperture, receiving input via a user input device from a clinical study participant corresponding to the identity of the clinical study participant, releasing the stored unconsumed consumable unit using a dispensing mechanism located within the housing to the clinical study participant via the delivery aperture upon verification of the identity of the clinical study participant, and receiving further input from the clinical study participant via the user input device in response to one or more questionnaires relating to consumption of the consumable unit.

Some implementations further comprise gathering data from the unconsumed consumable unit using a reader located in the housing. Some implementations further comprise receiving into a second compartment at least a portion of a consumed consumable unit via a spent unit aperture of the housing. Some implementations further comprise comprising gathering data from the consumed consumable unit using a reader located in the housing. In some implementations, the input corresponding to the identity of the clinical study participant comprises a user number or access code. In some implementations, the consumable unit comprises an aerosol delivery device. Some implementations further comprise controlling the dispensing mechanism according to a clinical study protocol. Some implementations further comprise displaying information to the clinical study participant via a display portion of the user input device. In some implementations, the information conveyed to the clinical study participant includes the one or more questionnaires relating to consumption of the consumable unit. Some implementations further comprise transferring data to a remote device.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to a clinical study product dispensing device configured to dispense one or more consumable units in a controlled manner. The clinical study product dispensing device is further configured to receive input from a clinical study participant in response to one or more questionnaires relating to consumption of the consumable unit. As used herein the term "consumable unit" is meant to relate to any product in which a substance is delivered into the human body. Such products may include, but need not be limited to, foods, pharmaceutical drugs, medical devices, radiation-emitting products, vaccines, cosmetics, and/or tobacco products, such as, for example, pills, tablets, lozenges, dissolvable strips, combustible cigarettes, and e-cigarettes, including heat-not-burn cigarettes, vapor cigarettes, and/or vapor cartridges. In addition, it should be noted that term "unconsumed consumable unit" is meant to relate to a consumable unit that has not been consumed by a user, and the term "consumed consumable unit" is meant to relate to any portion, or the whole of, a consumable unit after any portion of the consumable unit has been consumed by the user. As used herein the term "consumed consumable unit" may relate to a whole consumable unit or a portion thereof, and likewise, the term "unconsumed consumable unit" may relate to a whole consumable unit or a portion thereof.

Figure 1:
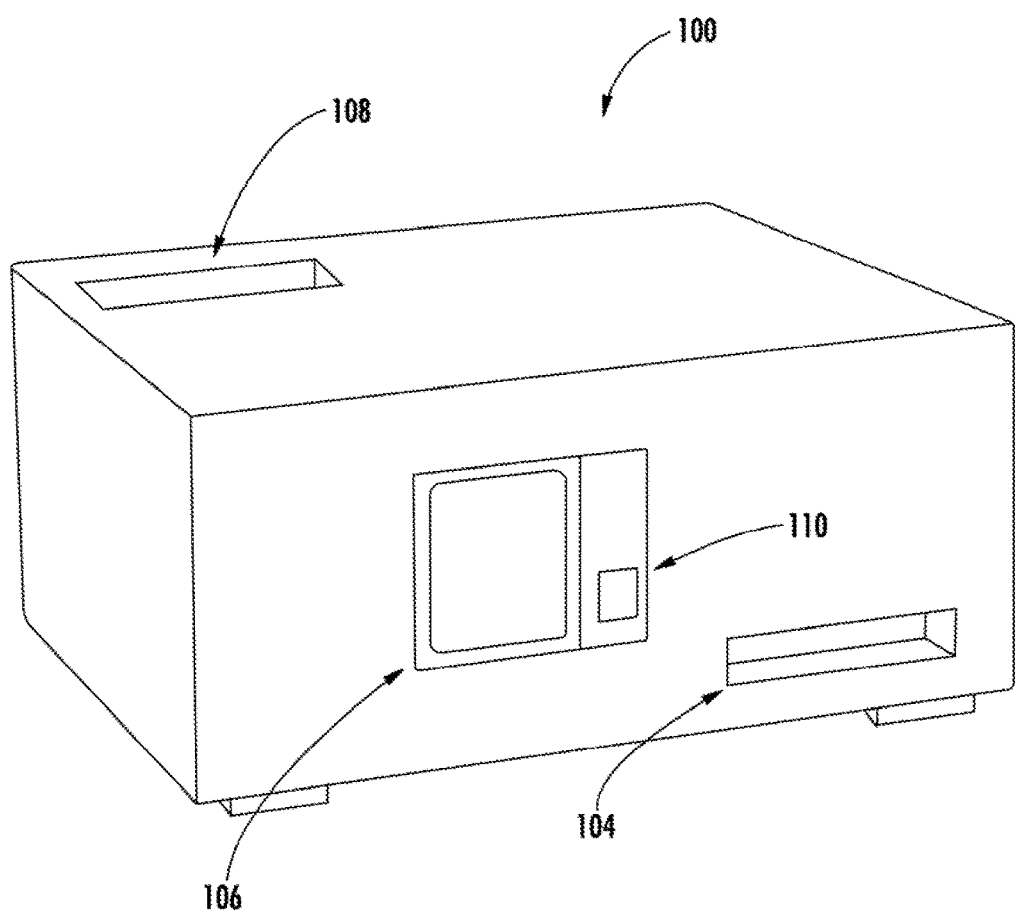
FIG. 1 illustrates a perspective view of a clinical study product dispensing device, according to an example implementation of the present disclosure.

FIG. 1 illustrates a perspective view of a clinical study product dispensing device, according to an example implementation of the present disclosure. In particular, FIG. 1 illustrates a clinical study product and storage device 100 that includes a housing 102, a delivery aperture 104, and a user input device 106. As will be discussed in more detail below, some implementations of the clinical study product dispensing device may further include a spent unit aperture 108. In various implementations, the housing of the clinical study product dispensing device may be constructed of one or more relatively sturdy materials, including, but not limited to various metal materials, including steel, as well as various plastic materials, including acrylonitrile butadiene styrene (ABS). In some implementations, the housing of the clinical study product dispensing device may be constructed of a combination of these materials.

Although in various implementations the size and shape of the housing of the clinical study product dispensing device may vary depending on the specific needs of the trial study and the consumable unit being studied, in some implementations the size and shape of the housing of the clinical study product dispensing device are designed such that the clinical study product dispensing device may be stocked by a representative associated with the trial study, and then transported home by the clinical study participant. In such a manner, the clinical study product storage and dispensing device may be used by the participant at that location and/or moved from location to location by the participant with relative ease. As such, the clinical study product dispensing device may be considered to be portable. Although not shown in the figures, in various implementations the clinical study product dispensing device may be lockable such that a representative associated with the trial study may lock the clinical study product dispensing device after the consumable units have been stocked in the device. Moreover, in various implementations the locking mechanism utilized by the clinical study product dispensing device may render the clinical study product dispensing device tamper-resistant and/or child-proof. Such locking mechanisms may include, but need not be limited to, various lock and key mechanisms, including a tubular cam lock, as well as various manual or electronic key and/or combination locks.

In various implementations, the user input device 106 can take a variety of forms, such as a button, keypad, dial, touch screen, audio input interface, visual/image capture input interface, input in the form of sensor data, etc. Still further, the user interface 106 may be configured to output information to the user through a display, speaker, or other output device. For example, in some implementations the user input device may comprise an electronic input device configured to receive various input commands from a participant and to provide output to the participant using an alpha-numeric keypad in combination with a display screen. In other implementations, the user input device may comprise a touchscreen, which functions as both an input and output device. Such touchscreens are commonly found in a variety of consumer devices such as smartphones, tablet computers, point of sale systems, automatic teller machines (ATMs), etc. In various implementations, the user input device may be configured to receive identification information from a clinical study participant. For example, in one implementation, a clinical study participant may enter a password, user number, access code, and/or other code associated with that particular clinical study participant via the user input device to provide the identification information. In the depicted implementation, the user input device includes a biometric reader 110. In some implementations, the biometric reader may exist in addition to the user input device. In general, a biometric reader is configured to verify and/or capture identifying information about a person based on physiological characteristics. Examples of suitable biometric readers include, but are not limited to, fingerprint readers and/or iris readers.

Figure 2:
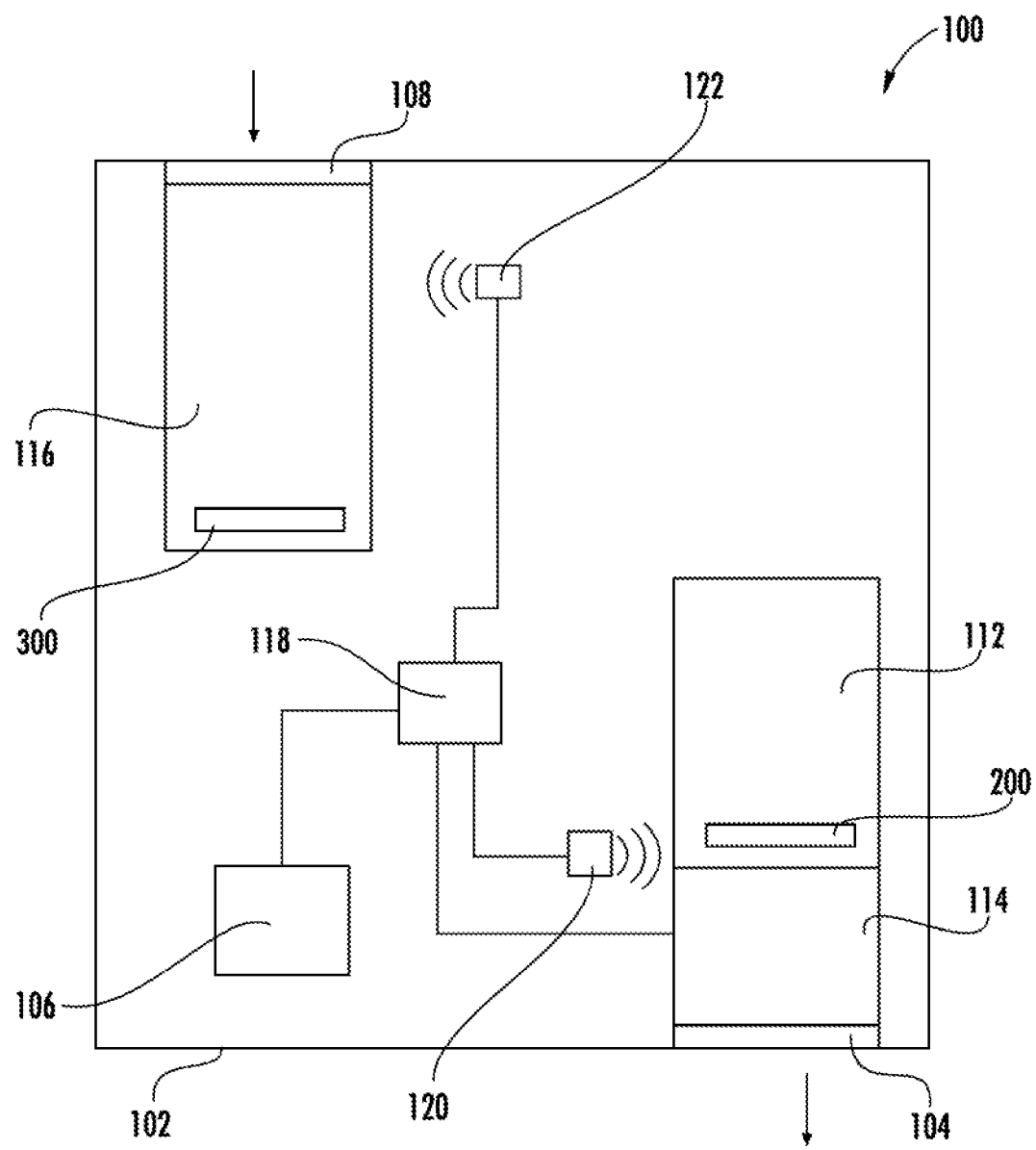
FIG. 2 is a schematic diagram of a clinical study product dispensing device, according to an example implementation of the present disclosure.

FIG. 2 illustrates a schematic diagram of the clinical study product dispensing device according to an example implementation of the present disclosure, showing additional components that may reside on or within the housing 102 of the device 100. In particular, FIG. 2 further illustrates a storage compartment 112, a dispensing mechanism 114, and a controller 118. In the depicted implementation, the storage compartment is located within the lockable housing 102, and the dispensing mechanism 114 is in mechanical association with the storage compartment 112 such that one or more consumable units 200 stocked in the storage compartment may be accessed by the dispensing mechanism 114 and delivered to the dispensing aperture 104 via control by the controller 118. In various implementations, the dispensing mechanism may be an electro-mechanical device. Such a mechanism may include, but need not be limited to, a belt system that is configured to receive an individual unconsumed consumable unit from the storage compartment and deliver it to the dispensing aperture, a gravity-assisted mechanism, such one that utilizes rollers, shutters, and/or blades to deliver an individual consumable unit to the dispensing aperture, and/or a mechanism employing a controlled spring or solenoid to eject a consumable unit into the dispensing aperture.

In the depicted implementation, the storage compartment 112 may be located within the lockable housing 102 of the clinical study product dispensing device and may be configured to be stocked with one or more consumable units prior to locking the housing and distribution of the device to a clinical study participant. In such a manner, a representative associated with the clinical study may ensure that the proper consumable unit or units are stocked in the device. In some implementations, the storage compartment may be an integral component of the interior of the housing, however, in other implementations the storage compartment may be removable, such that the storage compartment may be stocked with the one or more consumable units outside of the housing and then the stocked storage compartment may itself be inserted into the housing. Although not shown in the figures, in various implementations one or more sensors may be utilized to sense the presence of the consumable unit or units and/or the storage compartment itself. In various implementations, the storage compartment may be constructed of the same or a different material as the housing. In particular, the storage compartment may be constructed of one or more relatively sturdy materials, including, but not limited to various metal materials, including steel, as well as various plastic materials, including acrylonitrile butadiene styrene (ABS).

In addition to the controlled dispensing of a stored consumable unit, the implementations of the present disclosure depicted in FIGS. 1 and 2 are also configured to receive a portion (or all) of a consumable unit after it has been consumed by a clinical study participant via a spent consumable unit aperture 108 located in the housing 102. Such implementations may also include a spent consumable unit compartment 116 configured to store one or more spent consumable units. In the depicted implementation, the spent consumable unit storage compartment 116 may be located within the lockable housing 102 of the clinical study product dispensing device. In various implementations, the spent consumable unit storage compartment may be an integral component of the interior of the housing, however, in some implementations the spent consumable storage compartment may be removable. Although not shown in the figures, in various implementations one or more sensors may be utilized to sense the presence of a spent consumable unit or units and/or the spent consumable unit storage compartment itself. In various implementations, the spent consumable unit storage compartment may be constructed of the same or a different material as the housing. In particular, the spent consumable unit storage compartment may be constructed of one or more relatively sturdy materials, including, but not limited to various metal materials, including steel, as well as various plastic materials, including acrylonitrile butadiene styrene (ABS).

In various implementations, the clinical study product dispensing device may be configured to enable wireless communication. In some examples, a communication interface may be included on a printed circuit board (PCB) of the controller, or a separate PCB that may be coupled to the controller or one or more components of the controller. The communication interface may enable the clinical study product dispensing device to wirelessly communicate with one or more networks, computing devices or other appropriately-enabled devices. Examples of suitable computing devices include any of a number of different mobile computers. More particular examples of suitable mobile computers include portable computers (e.g., laptops, notebooks, tablet computers), mobile phones (e.g., cell phones, smartphones), wearable computers (e.g., smartwatches) and the like. In other examples, the computing device may be embodied as other than a mobile computer, such as in the manner of a desktop computer, server computer or the like. And in yet another example, the computing device may be embodied as an electric beacon such as one employing iBeacon™ technology developed by Apple Inc. Examples of suitable manners of wireless communication are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

The communication interface may include, for example, an antenna (or multiple antennas) and supporting hardware and/or software for enabling wireless communication with a communication network (e.g., a cellular network, Wi-Fi, WLAN, and/or the like), and/or for supporting device-to-device, short-range communication, in accordance with one or more desired communication technologies. The communication interface may at times be composed of multiple separate or integrated communication interfaces enabling communication in accordance with multiple communication technologies. Examples of suitable short-range communication technologies that may be supported by the communication interface include various near field communication (NFC) technologies, wireless personal area network (WPAN) technologies and the like. More particular examples of suitable WPAN technologies include those specified by IEEE 802.15 standards or otherwise, including Bluetooth, Bluetooth low energy (Bluetooth LE), ZigBee, infrared (e.g., IrDA), radio-frequency identification (RFID), Wireless USB and the like. Yet other examples of suitable short-range communication technologies include Wi-Fi Direct, as well as certain other technologies based on or specified by IEEE 802.11 standards and that support direct device-to-device communication.

As depicted in FIG. 2, the clinical study product dispensing device 100 may further include a stored consumable unit reader 120 coupled to the controller 118, which may be configured to enable wireless communication with a stored consumable unit. As such, the stored consumable unit reader 120 may communicate with a device located on a stored consumable unit 200 (or a portion thereof). The stored consumable unit reader 120 may include, for example, an antenna (or multiple antennas) and supporting hardware and/or software for enabling device-to-device, short-range communication in accordance with one or more desired communication technologies. Alternately, or in addition, the stored consumable unit reader 120 may enable wireless communication with a communication network (e.g., a cellular network, Wi-Fi, WLAN, and/or the like). The stored consumable unit reader 120 may at times be composed of multiple separate or integrated communication interfaces enabling communication in accordance with multiple communication technologies. Examples of suitable short-range communication technologies that may be supported by the communication interface include various near field communication (NFC) technologies, wireless personal area network (WPAN) technologies and the like. More particular examples of suitable WPAN technologies include those specified by IEEE 802.15 standards or otherwise, including Bluetooth, Bluetooth low energy (Bluetooth LE), ZigBee, infrared (e.g., IrDA), radio-frequency identification (RFID), Wireless USB and the like. Yet other examples of suitable short-range communication technologies include Wi-Fi Direct, as well as certain other technologies based on or specified by IEEE 802.11 standards and that support direct device-to-device communication.

In some implementations, the stored consumable unit reader may be configured to gather data from one or more stored consumable units. In various implementations the data may include, but need not be limited to, identification data and/or manufacturing data of the one or more stored consumable units. For example, in some implementations the stored consumable unit reader 120 may utilize RFID authentication as a means for authenticating one or more respective stored consumable units. To further illustrate aspects of example implementations of the present disclosure, reference is now made to FIG. 3, which illustrates various components for use within a clinical study product dispensing device, and more particularly for use in verifying one or more stored consumable units, and methods for operation of the various components.

Figure 3:
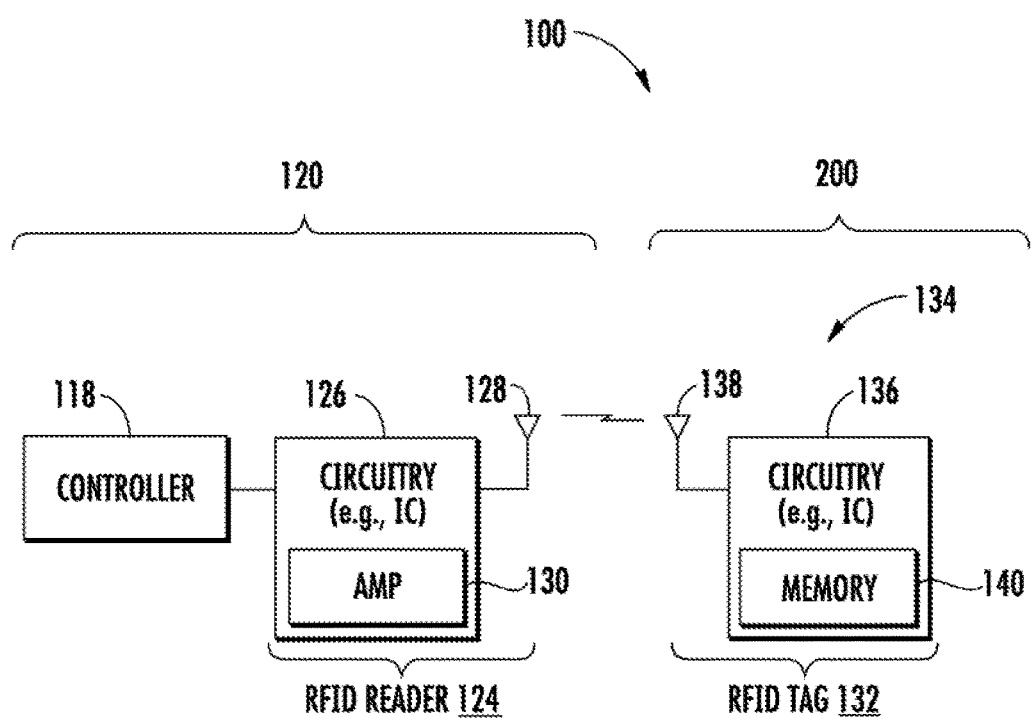
FIG. 3 illustrates an example configuration of various electronic components that may be within a clinical study product dispensing device to implement communication with a stored unconsumed consumable unit, according to an example implementation of the present invention.

FIG. 3 even more particularly illustrates various communication components of one implementation of the clinical study product dispensing device. As shown, these components may comprise the stored consumable unit reader 120, which may include an RFID reader 124. The RFID reader 124 may include circuitry 126, such as an integrated circuit (IC), coupled to an antenna 128, and having at least an amplifier 130 therein. In various implementations, the RFID reader may be coupled to the controller 118 of the clinical study storage and dispensing device. In one implementation, the amplifier 130 (e.g., a radio-frequency amplifier) is configured to drive the antenna 128. The amplifier may also be configured to operate at a sufficient power level to enable an emission of energy sufficient (e.g., at least one-hundred milliwatts) to at least partially power an RFID tag 132 contained within a stored consumable unit 200 when the stored consumable unit 200 (or a portion thereof) is in proximity of the reader 124. It should be noted that in other implementations, the amplifier may be configured to operate at a power level not explicitly expressed herein. For example, in one example implementation, the amplifier may also be configured to operate at a lower power level (e.g., less than one-hundred milliwatts). In some example implementations, the amplifier may be configured to operate within a constrained power level range (e.g., 10-20 milliwatts). In one implementation, for example, the amplifier may be configured to operate up to a predetermined number of milliwatts (e.g., 100 milliwatts).

As further shown, the stored consumable unit 200 (or a portion thereof) may comprise one or more electronic components 134 that may be, or include, an RFID tag 132 configured to communicate with the RFID reader 124 when the stored consumable unit 200 (or a portion thereof) is in proximity with the stored consumable unit reader 120. The RFID tag 132 may include circuitry 136 (e.g., IC) coupled to an antenna 138, and having at least a memory component 140 therein. In some example implementations, the clinical study product dispensing device, and more particularly the controller 118, may be configured to identify and/or capture data associated with a stored consumable unit 200 (or a portion thereof) prior to, or as, the stored consumable unit (or portion thereof) is dispensed by the dispensing mechanism 114 to the clinical study participant via the delivery aperture 104.

As previously indicated, the RFID reader 124 and the RFID tag 132 may include and/or be coupled with separate and distinct antennas 128, 138, respectively, in which that antennas may facilitate short-range communication between the RFID reader and the RFID tag. For example, the antenna 128 of the RFID reader 124 may be contained within the clinical study product dispensing device and coupled to the circuitry 126 of the RFID reader 124 such that upon storing and/or dispensing the stored consumable unit 200 (or portion thereof), the antenna 128 is located proximate the corresponding antenna 138 of the RFID tag 132 to enable the communication between the RFID reader 124 and the RFID tag 132.

In some example implementations, the antenna of the RFID reader may be coupled to a receiver within the circuitry of the RFID reader via one or more electronic components (e.g., a diode, a transistor, an optoelectronic device, a resistor, a capacitor, a switch, and the like). In various implementations, the receiver of the RFID tag 132 may receive the modulated signal communicated by the RFID reader 124 (e.g., communicated by a transmitter of the RFID reader) via the antenna 128, and thereby demodulate the signal. Examples of suitable receivers may be, or include, superheterodyne receivers and super-regenerative receivers. The receiver may be implemented alongside a protocol controller of the RFID tag that may receive and/or provide data to the receiver and memory 140. As such, in one example implementation, the protocol controller of the RFID tag may be operatively coupled to both the receiver and the memory.

In some example implementations, the antennas 128, 138 may be short in length (e.g., two millimeters in length) to render the RFID reader 124 and the RFID tag 132 substantially incapable of communication with any other device. However, it should be noted that in other implementations, the antennas may be a length that is not explicitly expressed herein. For example, in one example implementation, the antenna may be substantially longer (e.g., greater than two millimeters) in length. Generally, the antennas may be optimized to minimize the corresponding signal range thereby preventing undesired reading and/or writing communication to and from devices other than the RFID reader 124 and RFID tag 132 (including general RFID readers and RFID tags that are external to the clinical study product dispensing device). The antennas may be, or include, a monopole antenna, dipole antenna, differential antenna or other similarly appropriate antenna.

In alternate example implementations, the power emitted by either the RFID reader 124 and/or the RFID tag 132 may be limited to render the RFID reader and the RFID tag substantially incapable of communication with any other device. In one implementation, for example, the RFID tag may be solely powered via the RFID reader such that the power of the RFID reader may be limited thereby disabling an RFID tag that is external to the clinical study product dispensing device from being powered. In some example implementations, the RFID reader and/or the RFID tag may comprise integrated security parameters to prevent undesired reading and/or writing communication to and from devices other than the RFID reader 124 and RFID tag 132 (including general RFID readers and RFID tags that are external to the clinical study product dispensing device). In one implementation, for example, data stored within the RFID tag may be encrypted.

In some implementations, the communication between the RFID reader 124 and the RFID tag 132 may include transmitting and/or receiving data relating to verification of the stored consumable unit 200, such as, for example, verification indicia communicated from the RFID tag to the RFID reader. In some implementations, the communication between the RFID reader 124 and the RFID tag 132 may include verifying that the appropriate stored consumable unit 200 (or portion thereof) is dispensed to the appropriate clinical study participant according to a clinical study protocol. In some implementations, the communication may further include verifying that the stored consumable unit 200 (or portion thereof) is dispensed at the appropriate time and/or time interval, in accordance with a clinical study protocol. In various implementations, suitable verification of the stored consumable unit (or portion thereof) may comprise matching identity or designation information entered by a clinical study participant via the user input device 106 and identification information received by the stored consumable unit reader 120 associated with a stored consumable unit 200 (or portion thereof) with a clinical study protocol that, in some implementations, may be stored in a memory, such as, for example, a memory component of the controller 118. Upon verifying that the clinical study participant and the stored consumable unit 200 (or portion thereof) match the respective requirements in the clinical study protocol, the controller 118 may control the dispensing mechanism 114 to dispense the stored consumable unit 200 to the participant. For example, in one embodiment, a clinical study participant may enter his/her user number and/or access code into the user input device 106. Assuming the user number/access code is accepted, at that point the appropriate stored consumable unit may be dispensed and a time-stamp (which may include a date and/or time of day) may be recorded by the controller 118. The controller 118 may also trigger a series of timed questionnaires, which may follow an alert (such as, for example, a visual and/or audible alarm), to notify the clinical study participant that action is needed. In some embodiments, the clinical study participant may be required to re-enter his/her user number/access code before each response to the questionnaire(s).

In various implementations, the controller 118 may be configured to suspend and/or prevent dispensing of a stored consumable unit 200 (or portion thereof) based on the data received by the stored consumable unit reader 120. For example, if the identity of the stored consumable unit 200 (or portion thereof), and/or the identity or designation (such as, for example, the user number and/or access code) of the clinical study participant, does not match the respective requirements in the clinical study protocol, the controller 118 may be configured to suspend and/or prevent dispensing of a stored consumable unit (or portion thereof). Other implementations may allow dispensing of the stored consumable unit (or portion thereof), but may provide notification and/or other information to the clinical study participant regarding the dispensed consumable unit (or portion thereof) via a display that may be part of the user input device 106. In still other implementations, the controller 118 may be configured to send a notification to a clinician associated with the clinical study.

As also depicted in FIG. 2, the clinical study product dispensing device 100 may further include a consumed consumable unit reader 122 coupled to the controller 118, which may be configured to enable wireless communication. As such, the consumed consumable unit reader 122 may communicate with a device on a consumed consumable unit 300 (or portion thereof). The consumed consumable unit reader 122 may include, for example, an antenna (or multiple antennas) and supporting hardware and/or software for enabling device-to-device, short-range communication in accordance with one or more desired communication technologies. Alternately, or in addition, the consumed consumable unit reader 122 may enable wireless communication with a communication network (e.g., a cellular network, Wi-Fi, WLAN, and/or the like). The consumed consumable unit reader 122 may at times be composed of multiple separate or integrated communication interfaces enabling communication in accordance with multiple communication technologies. Examples of suitable short-range communication technologies that may be supported by the communication interface include various near field communication (NFC) technologies, wireless personal area network (WPAN) technologies and the like. More particular examples of suitable WPAN technologies include those specified by IEEE 802.15 standards or otherwise, including Bluetooth, Bluetooth low energy (Bluetooth LE), ZigBee, infrared (e.g., IrDA), radio-frequency identification (RFID), Wireless USB and the like. Yet other examples of suitable short-range communication technologies include Wi-Fi Direct, as well as certain other technologies based on or specified by IEEE 802.11 standards and that support direct device-to-device communication.

In some implementations, the consumed consumable unit reader 122 may be configured to gather data from one or more consumed consumable units. In various implementations the data may include, but need not be limited to, identification data and/or manufacturing data of the one or more consumed consumable units. For example, in some implementations the consumed consumable unit reader 122 may utilize RFID authentication as a means for authenticating one or more respective consumed consumable units according to the clinical study protocol. To further illustrate aspects of example implementations of the present disclosure, reference is now made to FIG. 4, which illustrates various components for use within a clinical study product dispensing device, and more particularly for use in reading one or more consumed consumable units, and methods for operation of the various components.

Figure 4:
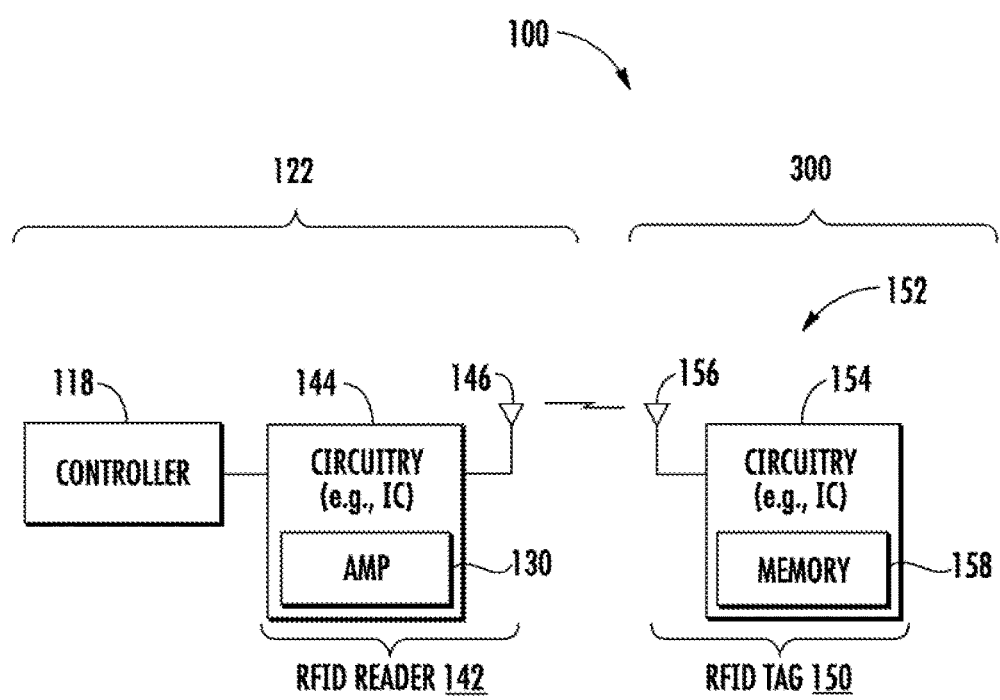
FIG. 4 illustrates an example configuration of various electronic components that may be within a clinical study product dispensing device to implement communication with a consumed consumable unit, according to an example implementation of the present invention.

FIG. 4 even more particularly illustrates various communication components of the clinical study product dispensing device. As shown, these components may comprise the consumed consumable unit reader 122, which may include an RFID reader 142. The RFID reader 142 may include circuitry 144, such as an integrated circuit (IC), coupled to an antenna 146, and having at least an amplifier 148 therein. In various implementations, the RFID reader 142 may be coupled to the controller 118. In one implementation, the amplifier 148 (e.g., a radio-frequency amplifier) is configured to drive the antenna 146. The amplifier may also be configured to operate at a sufficient power level to enable an emission of energy sufficient (e.g., at least one-hundred milliwatts) to at least partially power an RFID tag 150 contained within a consumed consumable unit 300 (or portion thereof) when the consumed consumable unit 300 (or a portion thereof) is in proximity of the reader 142. It should be noted that in other implementations, the amplifier may be configured to operate at a power level not explicitly expressed herein. For example, in one example implementation, the amplifier may also be configured to operate at a lower power level (e.g., less than one-hundred milliwatts). In some example implementations, the amplifier may be configured to operate within a constrained power level range (e.g., 10-20 milliwatts). In one implementation, for example, the amplifier may be configured to operate up to a predetermined number of milliwatts (e.g., 100 milliwatts).

As further shown, the consumed consumable unit 300 (or a portion thereof) may comprise one or more electronic components 152 that may be, or include, an RFID tag 150 configured to communicate with the RFID reader 142 when the consumed consumable unit 300 (or a portion thereof) is in proximity with the consumed consumable unit reader 122. The RFID tag may include circuitry 154 (e.g., IC) coupled to an antenna 156, and having at least a memory component 158 therein. In some example implementations, the clinical study product dispensing device, and more particularly the controller 118, may be configured to identify and/or capture data associated with a consumed consumable unit 300 (or portion thereof) after the consumed consumable unit 300 (or portion thereof) has been inserted into the clinical study product dispensing device 100 by the clinical study participant via the spent consumable unit aperture 108.

As previously indicated, the RFID reader 142 and the RFID tag 150 may include and/or be coupled with separate and distinct antennas 146, 152, respectively, in which that antennas may facilitate short-range communication between the RFID reader and the RFID tag. For example, the antenna 146 of the RFID reader may be contained within clinical study product dispensing device and coupled to the circuitry 144 of the RFID reader such that upon receiving a consumed consumable unit 300, the antenna 146 is located proximate a corresponding antenna 156 of the RFID tag to enable the communication between the RFID reader and the RFID tag.

In some example implementations, the antenna of the RFID reader may be coupled to a receiver within the circuitry of the RFID reader via one or more electronic components (e.g., a diode, a transistor, an optoelectronic device, a resistor, a capacitor, a switch, and the like). In various implementations, the receiver of the RFID tag 150 may receive the modulated signal communicated by the RFID reader 142 (e.g., communicated by a transmitter of the RFID reader) via the antenna 146, and thereby demodulate the signal. Examples of suitable receivers may be, or include, superheterodyne receivers and super-regenerative receivers. The receiver may be implemented alongside a protocol controller of the RFID tag that may receive and/or provide data to the receiver and memory 158. As such, in one example implementation, the protocol controller of the RFID tag may be operatively coupled to both the receiver and the memory.

In some example implementations, the antennas 146, 156 may be short in length (e.g., two millimeters in length) to render the RFID reader 142 and the RFID tag 150 substantially incapable of communication with any other device. However, it should be noted that in other implementations, the antennas may be a length that is not explicitly expressed herein. For example, in one example implementation, the antenna may be substantially longer (e.g., greater than two millimeters) in length. Generally, the antennas may be optimized to minimize the corresponding signal range thereby preventing undesired reading and/or writing communication to and from devices other than the RFID reader 142 and RFID tag 150 (including general RFID readers and RFID tags that are external to the clinical study product dispensing device). The antennas may be, or include, a monopole antenna, dipole antenna, differential antenna or other similarly appropriate antenna.

In alternate example implementations, the power emitted by either the RFID reader 142 and/or the RFID tag 150 may be limited to render the RFID reader and the RFID tag substantially incapable of communication with any other device. In one implementation, for example, the RFID tag may be solely powered via the RFID reader such that the power of the RFID reader may be limited thereby disabling an RFID tag that is external to clinical study product dispensing device from being powered. In some example implementations, the RFID reader and/or the RFID tag may comprise integrated security parameters to prevent undesired reading and/or writing communication to and from devices other than the RFID reader 142 and RFID tag 150 (including general RFID readers and RFID tags that are external to the clinical study product dispensing device). In one implementation, for example, data stored within the RFID tag may be encrypted.

In some implementations, the communication between the RFID reader 142 and the RFID tag 150 may include transmitting and/or receiving data relating to verification of the consumed consumable unit 300, such as, for example, verification indicia communicated from the RFID tag to the RFID reader. In some implementations, the communication between the RFID reader 142 and the RFID tag 150 may include verifying that the appropriate consumed consumable unit 300 (or portion thereof) was consumed by the clinical study participant according to a clinical study protocol. In various implementations, suitable verification of the consumed consumable unit (or portion thereof) may comprise matching identification information received by the consumed consumable unit reader 142 associated with a consumed consumable unit 300 (or portion thereof) with a clinical study protocol that, in some implementations, may be stored in a memory component of the controller 118. In various implementations, the controller 118 may be configured to suspend and/or prevent dispensing of a stored consumable unit 200 (or portion thereof) based on the data received by the consumed consumable unit reader 122. For example, if the identity of the consumed consumable unit 300 (or portion thereof) does not match the respective requirements in the clinical study protocol, the controller 118 may be configured to suspend and/or prevent dispensing of an additional stored consumable unit (or portion thereof). Other implementations may allow dispensing of an additional stored consumable unit (or portion thereof), but may send a notification to a clinician associated with the clinical study.

In various implementations, the controller 118 may be configured to convey information to the clinical study participant in response to identifying a consumed consumable unit 300 (or portion thereof) inserted into the clinical study storage and dispensing device. In some implementations this information or additional information may be conveyed after a specific time interval from dispensing a stored consumable unit 200 (or portion thereof), or after a specific time interval from receiving a consumed consumable unit 300 (or portion thereof). In various implementations, information may be conveyed to the clinical study participant by displaying the information on a display component of the user input device 106. In some implementations, the information may comprise a questionnaire relating to consumption of the consumed consumable unit received by the clinical study according to the clinical study protocol. Such questions may include, but need not be limited to, background information about the clinical study participant and/or an evaluation of the clinical study participant's experience with the consumable unit (e.g., On a scale of 1 to 10, how much did you like the consumable unit? On a scale of 1 to 10, how likely are you to use the consumable unit again?). Information may also be gathered relating to any adverse effects or events experienced by the clinical study participant during or after consuming the consumable unit.

As noted above, the present invention is configured for use with any consumable unit used by a clinical study participant. In one exemplary implementation, the consumable unit may comprise an aerosol delivery system. In various implementations, aerosol delivery systems according to the present disclosure use electrical energy to heat a material to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating components of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating component of the present disclosure can hold and use that component much like a smoker employs a traditional type of smoking article, for example, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as an aerosol delivery housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., a rechargeable battery and various electronics for controlling the operation of that article), and at the other end and integral with or removably coupled thereto, an outer body or shell containing a disposable portion (e.g., a disposable flavor-containing cartridge). Therefore, as used herein, the term consumable unit is meant to cover a reusable portion and a disposable portion together, and/or a reusable portion by itself, and/or a disposable portion by itself.

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouth end region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

In various examples, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate). A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein.

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., all of which are incorporated herein by reference in their entireties. See also, for example, the various types of smoking articles, aerosol delivery devices and electrically-powered heat generating sources referenced by brand name and commercial source in U.S. patent application Ser. No. 14/170,838 to Bless et al., filed Feb. 3, 2014, which is incorporated herein by reference in its entirety. Additionally, other types of smoking articles have been proposed in U.S. Pat. No. 5,505,214 to Collins et al., U.S. Pat. No. 5,894,841 to Voges, U.S. Pat. No. 6,772,756 to Shayan, U.S. Pat. App. Pub. No. 2006/0196518 to Hon, and U.S. Pat. App. Pub. No. 2007/0267031 to Hon, all of which are incorporated herein by reference in their entireties.

Figure 5:
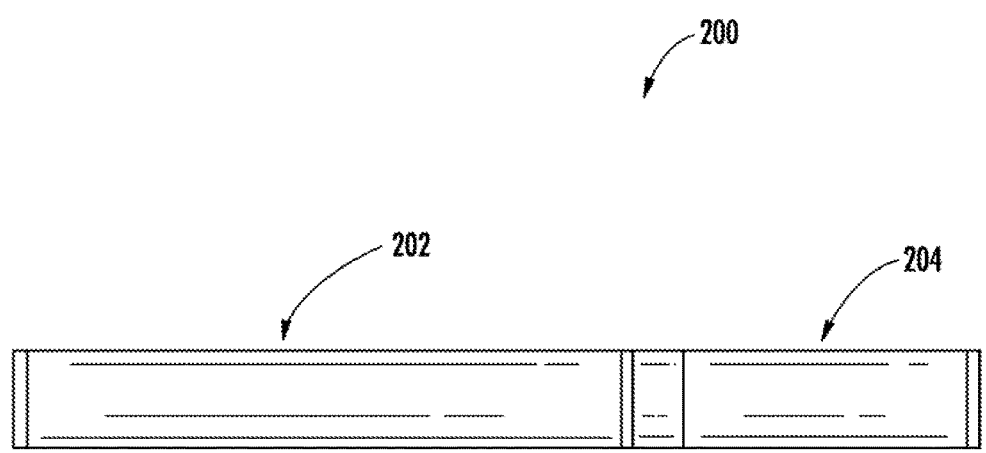
FIG. 5 is a side view of an aerosol delivery device including a cartridge coupled to a control body as may be used in conjunction with a clinical study product dispensing device, according to an example implementation of the present disclosure.

FIG. 5 illustrates a side view of an aerosol delivery device 200 including a control body 202 and a cartridge 204, according to various example implementations of the present disclosure. In particular, FIG. 5 illustrates the control body and the cartridge coupled to one another. The control body and the cartridge may be permanently or detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The cartridge and control body may include a unitary housing or outer body or separate, respective housings or outer bodies, which may be formed of any of a number of different materials. The housing may be formed of any suitable, structurally-sound material. In some examples, the housing may be formed of a metal or alloy, such as stainless steel, aluminum or the like.

Other suitable materials include various plastics (e.g., polycarbonate), metal-plating over plastic and the like.

In some example implementations, one or both of the control body 202 or the cartridge 204 of the aerosol delivery device 200 may be referred to as being disposable or as being reusable. For example, the control body may have a replaceable battery or a rechargeable battery and thus may be combined with any type of recharging technology, including connection to a typical alternating current electrical outlet, connection to a car charger (i.e., a cigarette lighter receptacle), and connection to a computer, such as through a universal serial bus (USB) cable or connector. Further, in some example implementations, the cartridge may comprise a single-use cartridge, as disclosed in U.S. Pat. No. 8,910, 639 to Chang et al., which is incorporated herein by reference in its entirety.

In one example implementation, the control body 202 and cartridge 204 forming the aerosol delivery device 200 may be permanently coupled to one another. Examples of aerosol delivery devices that may be configured to be disposable and/or which may include first and second outer bodies that are configured for permanent coupling are disclosed in U.S. patent application Ser. No. 14/170,838 to Bless et al., filed Feb. 3, 2014, which is incorporated herein by reference in its entirety. In another example implementation, the cartridge and control body may be configured in a single-piece, non-detachable form and may incorporate the components, aspects, and features disclosed herein. However, in another example implementation, the control body and cartridge may be configured to be separable such that, for example, the cartridge may be refilled or replaced.

Figure 6:
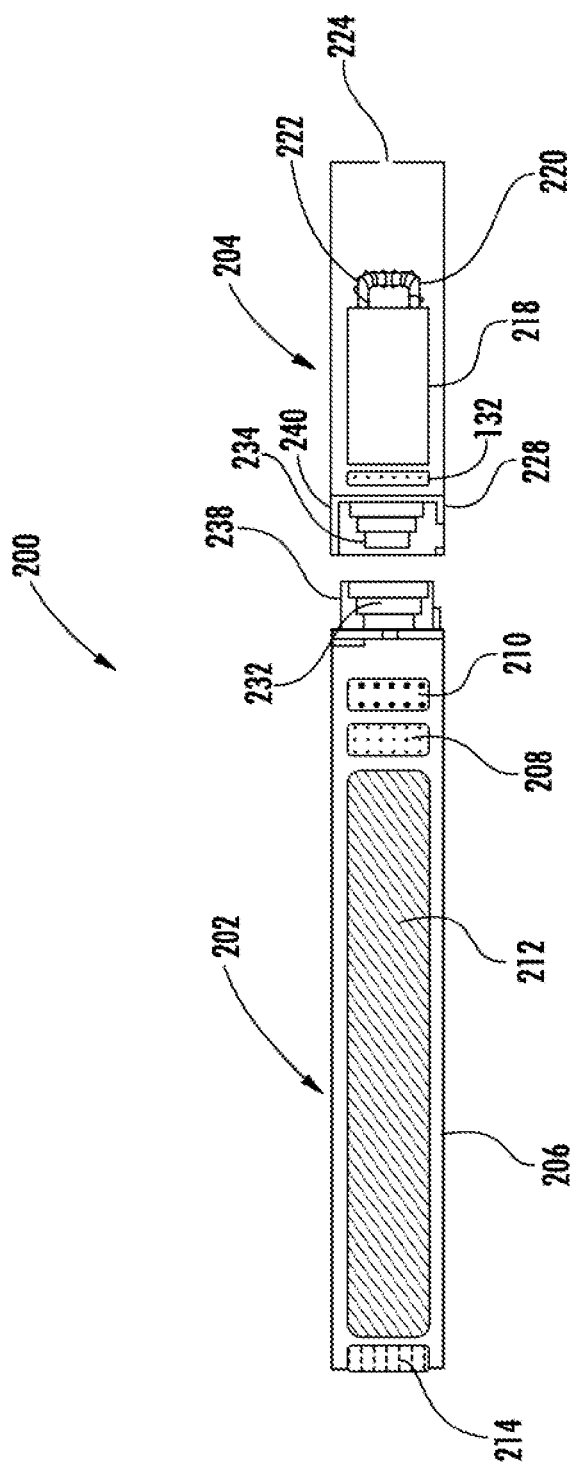
FIG. 6 is an exploded and sectioned side view of an aerosol delivery device including a cartridge coupled to a control body as may be used in conjunction with a clinical study product dispensing device, according to an example implementation of the present disclosure.

FIG. 6 illustrates a more particular example implementation of the aerosol delivery device 200. As seen in the cut-away view illustrated therein, the aerosol delivery device can comprise a control body 202 and cartridge 204. As illustrated in FIG. 5, the control body can be formed of a control body shell 206 that can include a control component 208 (e.g., a microprocessor, individually or as part of a microcontroller), a flow sensor 210, a battery 212, and one or more light-emitting diodes (LEDs) 214, and such components may be variably aligned. Further indicators (e.g., a haptic feedback component, an audio feedback component, or the like) can be included in addition to or as an alternative to the LED.

The cartridge 204 is formed of a cartridge shell 216 enclosing a reservoir 218 that is in fluid communication with a liquid transport element 220 adapted to wick or otherwise transport an aerosol precursor composition stored in the reservoir housing to a heater 222 (sometimes referred to as a heating element). In some example, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 222. The heater in these examples may be resistive heating element such as a wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as illustrated in FIG. 2A as described herein.

An opening 224 may be present in the cartridge shell 216 (e.g., at the mouthend) to allow for egress of formed aerosol from the cartridge 204. Such components are representative of the components that may be present in a cartridge and are not intended to limit the scope of cartridge components that are encompassed by the present disclosure.

The cartridge 204 also may include one or more electronic components, such an RFID tag 132 as described above, which may include an integrated circuit, a memory component, a sensor, or the like. In various implementations, the RFID tag 132 may be adapted to communicate with the controller 118 and/or with an external device by wired or wireless means. The electronic components may be positioned anywhere within the cartridge or a base 228 thereof. An example of an aerosol delivery system containing an RFID tag is described in U.S. Pat. App. Pub. No. 2017/0020191 to Lamb et al., which is incorporated herein by reference in its entirety.

Although the control component 208 and the flow sensor 210 are illustrated separately, it is understood that the control component and the flow sensor may be combined as an electronic circuit board with the air flow sensor attached directly thereto. Further, the electronic circuit board may be positioned horizontally relative to the illustration of FIG. 6 in that the electronic circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate as further described below.

The control body 202 and the cartridge 204 may include components adapted to facilitate a fluid engagement therebetween. As illustrated in FIG. 6, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the battery 212 and control component 208 in the control body and the heater 222 in the cartridge. Further, the control body shell 206 can include an air intake 236, which may be a notch in the shell where it connects to the coupler that allows for passage of ambient air around the coupler and into the shell where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference in its entirety. For example, the coupler 230 as seen in FIG. 6 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The aerosol delivery device 200 may be substantially rod-like or substantially tubular shaped or substantially cylindrically shaped in some examples. In other examples, further shapes and dimensions are encompassed—e.g., a rectangular or triangular cross-section, multifaceted shapes, or the like.

The reservoir 218 illustrated in FIG. 6 can be a container or can be a fibrous reservoir, as presently described. For example, the reservoir can comprise one or more layers of nonwoven fibers substantially formed into the shape of a tube encircling the interior of the cartridge shell 216, in this example. An aerosol precursor composition can be retained in the reservoir. Liquid components, for example, can be sorptively retained by the reservoir. The reservoir can be in fluid connection with the liquid transport element 220. The liquid transport element can transport the aerosol precursor composition stored in the reservoir via capillary action to the heater 222 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 6 as described herein. In particular, specific combinations of heating members and transport elements as further described below may be incorporated into devices such as illustrated in FIG. 6 as described herein.

In use, when a user draws on the aerosol delivery device 200, airflow is detected by the flow sensor 210, and the heater 222 is activated to vaporize components of the aerosol precursor composition. Drawing upon the mouthend of the aerosol delivery device causes ambient air to enter the air intake 236 and pass through the cavity 232 in the coupler 230 and the central opening in the projection 234 of the base 228. In the cartridge 204, the drawn air combines with the formed vapor to form an aerosol. The aerosol is whisked, aspirated or otherwise drawn away from the heater and out the opening 224 in the mouthend of the aerosol delivery device.

In some examples, the aerosol delivery device 200 may include a number of additional software-controlled functions. For example, the aerosol delivery device may include a battery protection circuit configured to detect battery input, loads on the battery terminals, and charging input. The battery protection circuit may include short-circuit protection and under-voltage lock out. The aerosol delivery device may also include components for ambient temperature measurement, and its control component 208 may be configured to control at least one functional element to inhibit battery charging if the ambient temperature is below a certain temperature (e.g., 0° C.) or above a certain temperature (e.g., 45° C.) prior to start of charging or during charging.

Power delivery from the battery 212 may vary over the course of each puff on the device 200 according to a power control mechanism. The device may include a "long puff" safety timer such that in the event that a user or an inadvertent mechanism causes the device to attempt to puff continuously, the control component 208 may control at least one functional element to terminate the puff automatically after some period of time (e.g., four seconds). Further, the time between puffs on the device may be restricted to less than a period of time (e.g., 100). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 210, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 200 may include a puff tracking algorithm configured for heater lockout once a defined number of puffs has been achieved for an attached cartridge (based on the number of available puffs calculated in light of the e-liquid charge in the cartridge). In some implementations, the puff tracking algorithm indirectly counts the number of puffs based on a corresponding number of puff seconds. As such, the puff tracking algorithm may incrementally count a number of puff seconds in order to calculate when a specified number of puffs have occurred and subsequently shut off the device once the puff seconds reach what is estimated to be a pre-determined number of puffs. For example, if three (3) seconds is defined to be equivalent to one "average" puff and the device have been configured to shut down after two hundred (200) average puffs, the device may shut down after six hundred (600) puff second have elapsed with respect to usage of the cartridge. The puff tracking algorithm may further estimate the amount of e-liquid that is utilized per puff second, and mathematically calculate the e-liquid volume based at least in part on the estimation of corresponding puffs seconds.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., which is incorporated herein by reference in its entirety.

The aerosol delivery device 200 can incorporate the sensor 210 or another sensor or detector for control of supply of electric power to the heater 222 when aerosol generation is desired (e.g., upon draw during use). As such, for example, there is provided a manner or method of turning off the power supply to the heater when the aerosol delivery device is not be drawn upon during use, and for turning on the power supply to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The aerosol delivery device 200 most preferably incorporates the control component 208 or another control mechanism for controlling the amount of electric power to the heater 222 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al., U.S. Pat. No. 5,101,839 to Jakob et al., U.S. Pat. No. 6,779,531 to Biggs et al., U.S. Pat. App. Pub. No. 2013/0008457 to Zheng et al., and *Chemical and Biological Studies on New Cigarette Prototypes that Heat Instead of Burn Tobacco*, R. J. Reynolds Tobacco Company Monograph (1988), all of which are incorporated herein by reference in their entireties.

Additional representative types of components that yield visual cues or indicators may be employed in the aerosol delivery device 200, such as LEDs and related components, auditory elements (e.g., speakers), vibratory elements (e.g., vibration motors) and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

The control component 208 includes a number of electronic components, and in some examples may be formed of a printed circuit board (PCB) that supports and electrically connects the electronic components. Examples of suitable electronic components include a microprocessor or processor core, an integrated circuit, a memory, and the like. In some examples, the control component may include a microcontroller with an integrated processor core and memory, and which may further include one or more integrated input/output peripherals.

In various implementations, the RFID tag 132 may be configured to communicate with a clinical study product dispensing device. For example, in various implementations the RFD tag 132 of the cartridge 204 may communicate with the clinical study product dispensing device 100 via communication with the RFID reader 124 of the stored consumable unit reader 120, as described above. As noted, the RFID tag may include circuitry 136 (e.g., IC) coupled to an antenna 138, and having at least a memory component 140 therein. The RFID reader 124 and the RFID tag 132 may include and/or be coupled with separate and distinct antennas 128, 138, respectively, in which that antennas may facilitate short-range communication between the RFID reader and the RFID tag. For example, the antenna 128 of the RFID reader may be coupled to the circuitry 126 of the RFID reader such that upon storing and/or dispensing a consumable unit, or prior to dispensing a consumable unit, the antenna 128 of the RFD reader may be located proximate a corresponding antenna 138 of the RFID tag 132 to enable the communication between the RFID reader 124 and the RFID tag 132.

In some example implementations, the antenna 128 of the RFID reader 124 may be coupled to the amplifier 130 and a transmitter within the circuitry of the RFID reader. The transmitter of the RFID reader may be or include a circuitry component capable of transmitting and modulating radio waves to communicate data via the RFID reader to the RFID tag 132. The transmitter may be implemented alongside a protocol controller that may provide data to the transmitter for subsequent communication in which the data may be received from the controller 118. As such, in some example implementations, the control component is operatively coupled to the circuitry of the RFID reader via the protocol controller.

The antenna 138 of the RFID tag 132 may be contained within the housing of the cartridge 204 and coupled to the circuitry 136 of the RFID tag such that when the antenna 138 of the RFD tag 132 is located proximate the corresponding antenna 128 of the RFID reader 124, communication is enabled between the RFID reader and the RFID tag. In some example implementations, the antenna of the RFID reader may be coupled to a receiver within the circuitry of the RFID reader via one or more electronic components (e.g., a diode, a transistor, an optoelectronic device, a resistor, a capacitor, a switch, and the like).

The receiver of the RFID tag 132 may receive the modulated signal communicated by the RFID reader 306 (e.g., communicated by a transmitter of the RFID reader) via the antenna 138, and thereby demodulate the signal. Examples of suitable receivers may be, or include, superheterodyne receivers and super-regenerative receivers. The receiver may be implemented alongside a protocol controller of the RFID tag that may receive an/or provide data to the receiver and memory 140. As such, in one example implementation, the protocol controller of the RFID tag may be operatively coupled to both the receiver and the memory.

In some example implementations, the antennas 128, 138 may be short in length (e.g., two millimeters) to render the RFID reader 124 and the RFID tag 132 substantially incapable of communication with any other device. However, it should be noted that in other implementations, the antenna may be a length that is not explicitly expressed herein. For example, in one example implementation, the antenna may be substantially longer (e.g., greater than two millimeters) in length. Generally, the antennas may be optimized to minimize the corresponding signal range thereby preventing undesired reading and/or writing communication to and from devices other than the RFID reader 124 and RFID tag 132 (including general RFID readers and RFID tags that are external to the aerosol delivery device 100). The antennas may be, or include, a monopole antenna, dipole antenna, differential antenna or other similarly appropriate antenna.

In alternate example implementations, the power emitted by either the RFID reader 124 and/or the RFID tag 132 may be limited to render the RFID reader and the RFID tag substantially incapable of communication with any other device. In one implementation, for example, the RFID tag may be solely powered via the RFID reader such that the power of the RFID reader may be limited thereby disabling an RFID tag that is external to the aerosol delivery device 100 from being powered.

Figure 7:
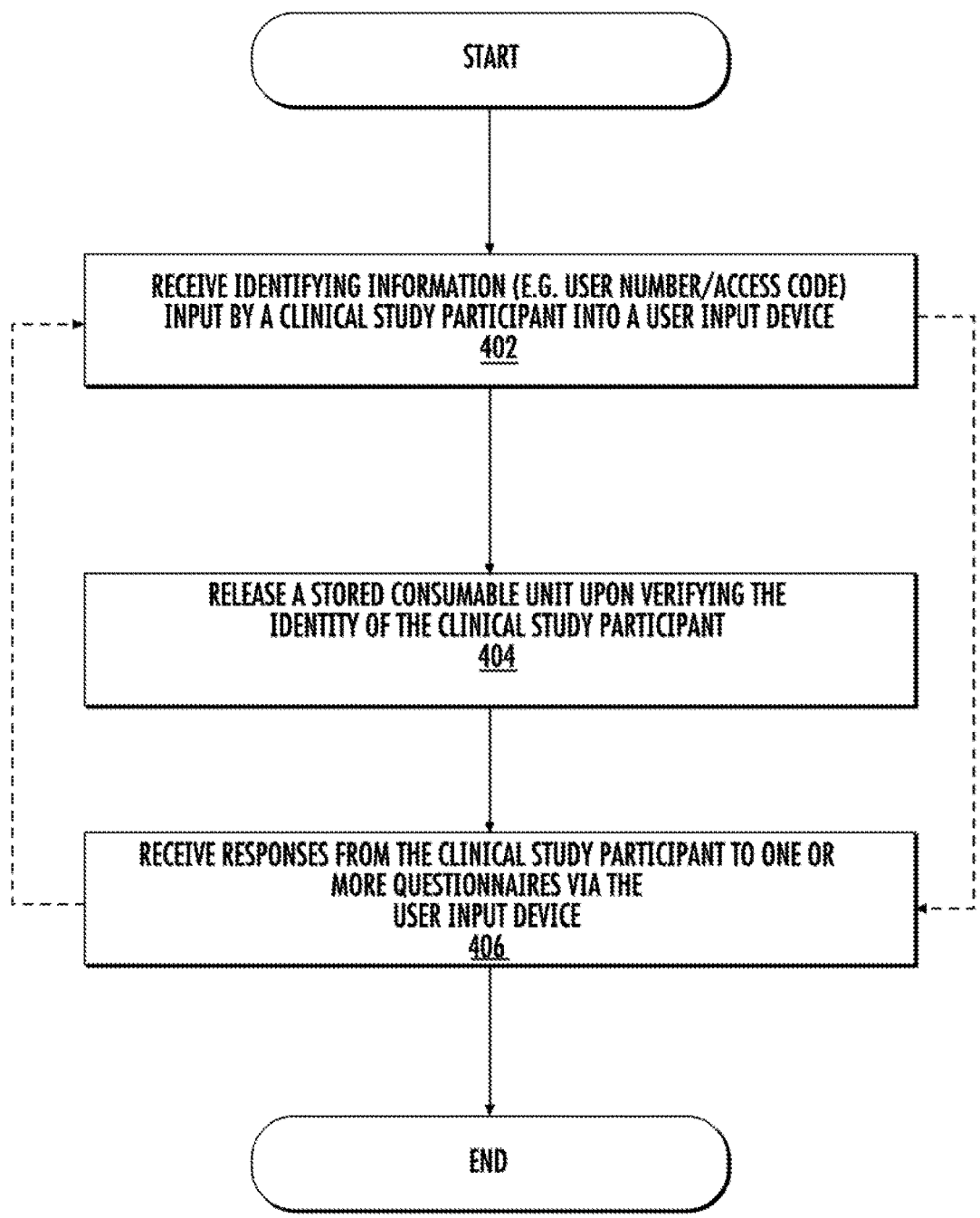
FIG. 7 illustrates various operations in a method of operation of a clinical study product dispensing device, according to an example implementation of the present disclosure.

FIG. 7 illustrates various operations in a method 400 of operation of the clinical study product dispensing device in accordance with an example implementation of the present disclosure. As shown at block 402, the method may include receiving identification information input by a user, such as a clinical trial participant, into a user input device of a clinical study product dispensing device. As shown at block 404, the method may also include releasing a stored unconsumed consumable unit to the clinical trial participant upon verification of the identity of the clinical trial participant. As shown at block 406, the method may further include receiving responses to one or more questionnaires relating to consumption of the consumable unit input by the user via the user input device. As noted above, in various implementations these questionnaires may occur in response to receiving a consumed consumable unit and/or after a time interval according to a clinical study protocol. In various implementations, some or all of this method may be repeated for additional consumable units according to the clinical study protocol. Various implementations may also include additional, or substituted, steps as described with respect to the storage and dispensing device above. Such steps may include, but need not be limited to, gathering data from an unconsumed consumable unit using a reader located in the housing, and/or receiving into a compartment at least a portion of a consumed consumable unit via a spent unit aperture of the housing, and/or gathering data from a consumed consumable unit using a reader located in the housing.

Figure 8:
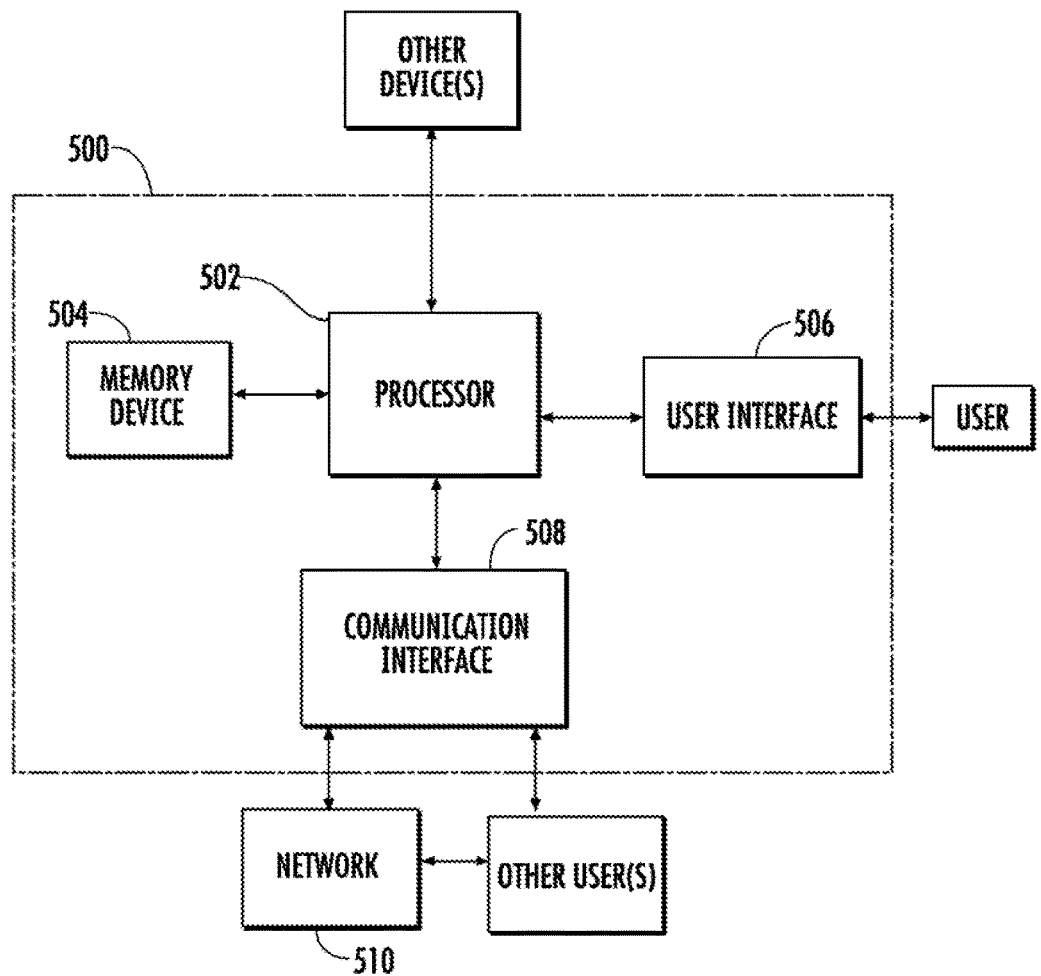
FIG. 8 illustrates a schematic diagram of a controller according to an example implementation of the present disclosure.

FIG. 8 shows a schematic view of a controller 500 (such as, for example, controller 118 of the clinical study product dispensing device 100 described above) in accordance with an example implementation of the present disclosure. As illustrated in FIG. 8, the controller 500 may be configured to execute computer code for performing the operations described herein. In this regard, as illustrated in FIG. 8, the controller 500 may comprise a processor 502 that may be a microprocessor or a controller for controlling the overall operation thereof. In one implementation the processor 502 may be particularly configured to execute program code instructions related to the functions described herein, including the operations for dispensing consumable units, receiving consumable units, or portions thereof of the present disclosure. The controller 500 may also include a memory device 504. The memory device 504 may include non-transitory and tangible memory that may be, for example, volatile and/or non-volatile memory. The memory device 504 may be configured to store information, data, files, applications, instructions or the like. For example, the memory device 504 could be configured to buffer input data for processing by the processor 502. Additionally or alternatively, the memory device 504 may be configured to store instructions for execution by the processor 502. As described above, the controller 500 may be connected to one or more additional devices (such as in the case of controller 118 of the clinical study product dispensing device 100, a dispending device 114, a stored consumable unit reader 120, and/or a consumed consumable unit reader 122).

As noted above, the controller 500 may be connected to a user interface 506 (such as, for example, the user input device 106 of the clinical study product dispensing device 100 as described above) that allows a user to interact therewith. As noted, the user interface can take a variety of forms, such as a button, keypad, dial, touch screen, audio input interface, visual/image capture input interface, input in the form of sensor data, etc. Still further, the user interface may be configured to output information to the user through a display, speaker, or other output device. A communication interface 508 may provide for transmitting and receiving data through, for example, a wired or wireless network 510 such as a local area network (LAN), a metropolitan area network (MAN), and/or a wide area network (WAN), for example, the Internet. The communication interface 508 may enable the controller 500 to communicate with one or more further computing devices, either directly, or via the network 510. In the example implementation of the clinical study product dispensing device 100 described above, this may enable communication between the device 100 and a remote device, such as a device accessible by a clinician associated with the clinical study, such that the clinician may monitor use of the device 100 and/or the consumable unit(s). In this regard, the communication interface 508 may include one or more interface mechanisms for enabling communication with other devices and/or networks. The communication interface 508 may accordingly include one or more interface mechanisms, such as an antenna (or multiple antennas) and supporting hardware and/or software for enabling communications via wireless communication technology (e.g., a cellular technology, communication technology, Wi-Fi and/or other IEEE 802.11 technology, Bluetooth, Zigbee, wireless USB, NFC, RF-ID, WiMAX and/or other IEEE 802.16 technology, and/or other wireless communication technology) and/or a communication modem or other hardware/software for supporting communication via cable, digital subscriber line (DSL), USB, FireWire, Ethernet, one or more optical transmission technologies, and/or other wireline networking methods. Non-limiting examples of communication protocols that may be used according to the present disclosure are described in U.S. patent application Ser. No. 14/327,776 to Ampolini et al., filed Jul. 10, 2014, which is incorporated herein by reference in its entirety.

The various aspects, embodiments, implementations or features of the described embodiments can be used separately or in any combination. Various aspects of the described implementations can be implemented by software, hardware or a combination of hardware and software. The described implementations can also be embodied as computer readable code on a computer readable medium for controlling the above-described operations. In particular, computer readable code may be configured to perform each of the operations of the methods described herein and embodied as computer readable code on a computer readable medium for controlling the above-described operations. In this regard, a computer readable storage medium, as used herein, refers to a non-transitory, physical storage medium (e.g., a volatile or non-volatile memory device, which can be read by a computer system. Examples of the computer readable medium include read-only memory, random-access memory, CD-ROMs, DVDs, magnetic tape, and optical data storage devices. The computer readable medium can also be distributed over network-coupled computer systems so that the computer readable code is stored and executed in a distributed fashion.

As noted above, the controller 500 may be configured to execute computer code for performing the above-described operations. In this regard, an implementation of a non-transitory computer readable medium for storing computer instructions executed by a processor in a controller (e.g. controller 500) configured to dispense consumable units is provided. The non-transitory computer readable medium may comprise program code instructions for storing an unconsumed consumable unit inside a compartment of a housing that includes a delivery aperture; program code instructions for receiving input via a user input device from a clinical study participant corresponding to the identity of the clinical study participant; program code instructions for releasing the stored unconsumed consumable unit using a dispensing mechanism located within the housing to the clinical study participant via the delivery aperture upon verification of the identity of the clinical study participant; and program code instructions for receiving further input from the clinical study participant via the user input device in response to one or more questionnaires relating to consumption of the consumable unit. In some implementations, the non-transitory computer readable medium may comprise further program code instructions for gathering data from the unconsumed consumable unit using a reader located in the housing. In some implementations, the non-transitory computer readable medium may further comprise program code instructions for receiving into a second compartment at least a portion of a consumed consumable unit via a spent unit aperture of the housing. In some implementations, the non-transitory computer readable medium may comprise further program code instructions for gathering data from the consumed consumable unit using a reader located in the housing. In some implementations, the non-transitory computer readable medium may comprise further program code instructions for receiving biometric information from a user via the user input device. In some implementations, the non-transitory computer readable medium may comprise further program code instructions for controlling the dispensing mechanism according to a clinical study protocol. In some implementations, the non-transitory computer readable medium may comprise further program code instructions for displaying information to the clinical study participant via a display portion of the user input device. In some implementations, the non-transitory computer readable medium may comprise further program code instructions for displaying one or more questionnaires relating to consumption of the consumable unit. In some implementations, the non-transitory computer readable medium may comprise further program code instructions for transferring of data to a remote device.

Figure 9:
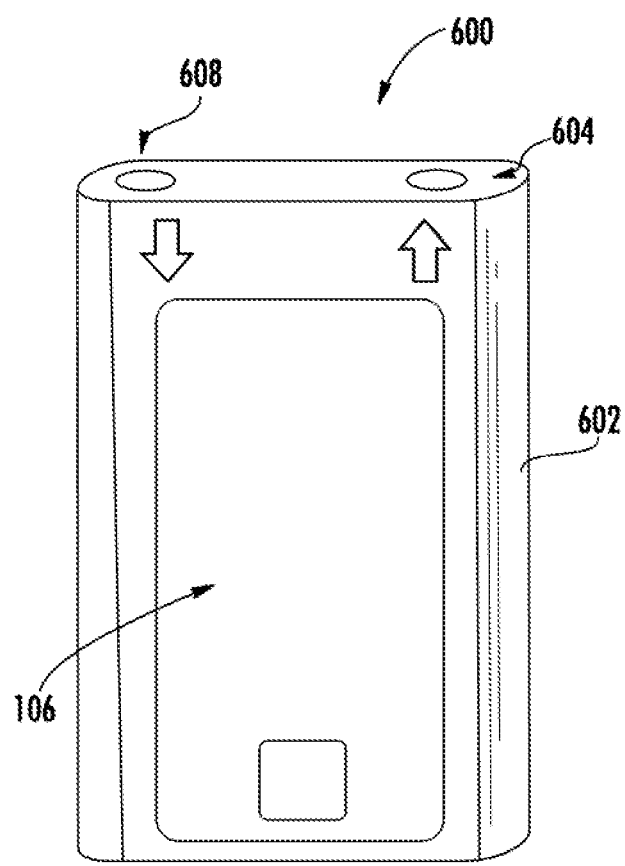
FIG. 9 a perspective view of a hand-held clinical study product dispensing device, according to an example implementation of the present disclosure.

FIG. 9 illustrates a perspective view of a clinical study product dispensing device 600 according to another example implementation of the present disclosure. In particular, FIG. 9 illustrates a hand-held version of the device. As such, the device 600 is configured to be operated while being held in a user's hand. As shown in FIG. 9, the clinical study product dispensing device 600 of the depicted implementation includes a housing 602, a delivery aperture 604, and a user input device 606. The device 600 of the depicted implementation further includes a spent unit aperture 608. The device 600 shown in FIG. 9 is similar in function to the device 100 described above, however the housing 602 of the device 600 is configured to fit in a user's hand. In various implementations, the device 600 may also include a battery power source. In some implementations, the battery power source may comprise a rechargeable battery configured to provide power to the dispensing mechanism, the under input device, and the controller. The various components of the device as described above are configured to fit within the housing 600. It should therefore be understood that the explanations above regarding the various components of the clinical trial product dispensing device, and the functions and capabilities thereof, are equally applicable to the device 600.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-9 or as otherwise described above may be included in an aerosol delivery device according to the present disclosure.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A dispensing device for use in studying a consumable unit used by a clinical study participant, said device comprising:

a housing that includes a delivery aperture and a compartment configured to store an unconsumed consumable unit therein;

a user input device configured to receive input from the clinical study participant corresponding to the identity of the clinical study participant;

a dispensing mechanism located within the housing and configured to release the stored unconsumed consumable unit to the clinical study participant via the delivery aperture upon verification of the identity of the clinical study participant; and a controller configured to interface with the dispensing mechanism and the user input device, wherein the user input device is further configured to receive input from the clinical study participant in response to one or more questionnaires relating to consumption of the consumable unit.

2. The dispensing device of claim 1, further comprising a reader located in the housing configured to gather data from the unconsumed consumable unit.

3. The dispensing device of claim 1, wherein the housing further includes a spent unit aperture and a second compartment configured to receive at least a portion of a consumed consumable unit via the spent unit aperture.

4. The dispensing device of claim 3, further comprising a reader located in the housing and configured to gather data from the consumed consumable unit.

5. The dispensing device of claim 1, wherein the input corresponding to the identity of the clinical study participant comprises a user number or access code.

6. The dispensing device of claim 1, wherein the consumable unit comprises an aerosol delivery device.

7. The dispensing device of claim 1, wherein the controller is further configured to control the dispensing mechanism according to a clinical study protocol.

8. The dispensing device of claim 1, wherein the user input device further comprises a display configured to display information to the clinical study participant.

9. The dispensing device of claim 8, wherein the information conveyed to the clinical study participant includes the one or more questionnaires relating to consumption of the consumable unit.

10. The dispensing device of claim 1, wherein the controller is further configured to control transfer of data to a remote device.

11. The dispensing device of claim 1, wherein the device is configured to be hand-held.

12. The dispensing device of claim 11, further comprising a rechargeable battery configured to provide power to the dispensing mechanism, the user input device, and the controller.

13. A method of operating a dispensing device for use in studying a consumable unit used by a clinical study participant, said method comprising:
 storing an unconsumed consumable unit inside a compartment of a housing that includes a delivery aperture;
 receiving input via a user input device from a clinical study participant corresponding to the identity of the clinical study participant;
 releasing the stored unconsumed consumable unit using a dispensing mechanism located within the housing to the clinical study participant via the delivery aperture upon verification of the identity of the clinical study participant; and
 receiving further input from the clinical study participant via the user input device in response to one or more questionnaires relating to consumption of the consumable unit.

14. The method of claim 13, further comprising gathering data from the unconsumed consumable unit using a reader located in the housing.

15. The method of claim 13, further comprising receiving into a second compartment at least a portion of a consumed consumable unit via a spent unit aperture of the housing.

16. The method of claim 15, further comprising gathering data from the consumed consumable unit using a reader located in the housing.

17. The method of claim 13, wherein the input corresponding to the identity of the clinical study participant comprises a user number or access code.

18. The method of claim 13, wherein consumable unit comprises an aerosol delivery device.

19. The method of claim 13, further comprising controlling the dispensing mechanism according to a clinical study protocol.

20. The method of claim 13, further comprising displaying information to the clinical study participant via a display portion of the user input device.

21. The method of claim 20, wherein the information conveyed to the clinical study participant includes the one or more questionnaires relating to consumption of the consumable unit.

22. The method of claim 13, further comprising transferring data to a remote device.

\* \* \* \* \*